(12) United States Patent
Cole et al.

(10) Patent No.: US 6,189,388 B1
(45) Date of Patent: Feb. 20, 2001

(54) ACCESS FLOW MONITORING USING REVERSAL OF NORMAL BLOOD FLOW

(75) Inventors: Eugene Cole, Englewood, CO (US); James Brugger, Newburyport, MA (US)

(73) Assignee: Gambro, Inc., Lakewood, CO (US)

(*) Notice: Under 35 U.S.C. 154(b), the term of this patent shall be extended for 0 days.

(21) Appl. No.: 08/976,325

(22) Filed: Nov. 12, 1997

(51) Int. Cl.[7] ............................................. G01F 1/704
(52) U.S. Cl. ........................................................ 73/861.07
(58) Field of Search .......................... 73/861.07, 861.11, 73/861.08, 861.16; 324/445, 722; 604/52; 600/584

(56) References Cited

U.S. PATENT DOCUMENTS

| | | |
|---|---|---|
| 2,709,785 | 5/1955 | Fielden . |
| 3,324,720 | 6/1967 | Sutherland . |
| 3,396,331 | 8/1968 | Sperry, IIII . |
| 3,404,336 | 10/1968 | Rosenthal . |
| 3,450,984 | 6/1969 | Holmes . |
| 3,482,575 | 12/1969 | Claff et al. . |
| 3,491,592 | 1/1970 | Evers et al. . |
| 3,619,423 | 11/1971 | Galletti et al. . |
| 3,722,276 | 3/1973 | Chandler et al. . |
| 3,867,688 | 2/1975 | Koski . |
| 3,980,946 | 9/1976 | Fleury . |
| 3,985,134 | 10/1976 | Lissot et al. . |
| 3,987,788 | 10/1976 | Emil . |
| 4,081,372 | 3/1978 | Atkin et al. . |
| 4,136,563 | 1/1979 | Mueller et al. . |
| 4,138,639 | 2/1979 | Hutchins . |
| 4,181,610 | 1/1980 | Shintani et al. . |
| 4,361,049 | 11/1982 | Volgyesi . |
| 4,446,871 | 5/1984 | Imura . |
| 4,508,622 | 4/1985 | Polaschegg et al. . |
| 4,650,458 | 3/1987 | Dahlberg et al. . |
| 4,715,849 | * 12/1987 | Gion et al. ............................. 604/52 |
| 4,739,492 | 4/1988 | Cochran . |

(List continued on next page.)

FOREIGN PATENT DOCUMENTS

| | | |
|---|---|---|
| 0097366 | 1/1984 | (EP) . |
| 0272414 | 6/1988 | (EP) . |
| 0693296A1 | 1/1996 | (EP) . |
| 0773035A3 | 11/1997 | (EP) . |
| 0845273A1 | 6/1998 | (EP) . |
| 2026508 | 5/1992 | (ES) . |
| 52-36990 | of 1977 | (JP) . |
| 60-190873 | of 1985 | (JP) . |
| WO 97/10013 | 3/1997 | (WO) . |
| WO 99/64088 | 12/1999 | (WO) . |

OTHER PUBLICATIONS

Robert L. Hester, Ph.D., "A New Technique for Determining Recirculation in the ESRD Patient", Nephrology News & Issues, pp. 44–55, Jun. 1993, Jackson, MS.

Gambro, "FAM 10 Fistula Flow Studies and Their Interpretation", pp. 1–31, Lund Sweden, published on or before Sep. 29, 1991.

(List continued on next page.)

*Primary Examiner*—Benjamin R. Fuller
*Assistant Examiner*—Jewel V. Thompson
(74) *Attorney, Agent, or Firm*—Edna M. O'Connor; Peter B Scull; Bruce R. Winsor (57) ABSTRACT

A method and apparatus in which the blood flow in a fistula is determined by comparing the property of blood entering the fistula to the property of blood being withdrawn from the fistula as the blood in the fistula flows in the direction which is the reverse of the predominant flow. A property marker fluid is injected into the blood entering the fistula in order to alter the property of the blood. Aseptic conditions are maintained during the reversal of the blood flow by maintaining a closed blood loop exterior to the patient. The blood loop closure is maintained by reversing the action of the pump which induces blood flow in the closed blood loop.

39 Claims, 6 Drawing Sheets

U.S. PATENT DOCUMENTS

| | | |
|---|---|---|
| 4,740,755 | 4/1988 | Ogawa . |
| 4,825,168 | 4/1989 | Ogawa et al. . |
| 4,995,268 | 2/1991 | Ash et al. . |
| 5,004,459 | 4/1991 | Peabody et al. . |
| 5,024,756 | 6/1991 | Sternby . |
| 5,092,836 | 3/1992 | Polashegg . |
| 5,098,373 | 3/1992 | Polaschegg . |
| 5,312,550 | 5/1994 | Hester . |
| 5,372,136 | 12/1994 | Steuer et al. . |
| 5,442,969 | 8/1995 | Troutner et al. . |
| 5,453,576 | 9/1995 | Krivitski . |
| 5,507,723 | 4/1996 | Keshaviah . |
| 5,510,716 | 4/1996 | Buffaloe, IV et al. . |
| 5,510,717 * | 4/1996 | Buffaloe, IV et al. ............. 324/445 |
| 5,518,623 | 5/1996 | Keshaviah et al. . |
| 5,588,959 | 12/1996 | Ahmad et al. . |
| 5,595,182 | 1/1997 | Krivitski . |
| 5,605,630 | 2/1997 | Shibata . |
| 5,662,806 | 9/1997 | Keshaviah et al. . |
| 5,685,989 | 11/1997 | Krivitski et al. . |
| 5,830,365 | 11/1998 | Schneditz . |
| 5,866,015 | 2/1999 | Krämer . |
| 5,902,253 * | 5/1999 | Pfeiffer et al. ....................... 600/584 |

OTHER PUBLICATIONS

Salamon et al. Translation: low frequency electrodeless conductometer for measuring the electrical conductivity of solutions, 1959, Industrial Group Headquarters, Risley, Warrington, Lancashire, GB.

Richard A. Sherman, "Recirculation Revisited", Seminars in Dialysis, vol. 4, No. 4 pp. 221–223, Oct.–Dec. 1991, New Jersey.

McKamy Smith, "Cardiac Output Determined by the Saline Conductivity Method Using an Extraarterial Conductivity Cell", Cardiovascular Research Center Bulletin, vol. 5, No. 4, pp. 123–134, Apr.–Jun. 1967, Texas.

Mogens Thomsen et al., "Evaluation of Clinical Examination Preceding Surgical Treatment of AV–Fistula Problems," Acta Chir Scand, vol. 151, pp. 133–137, 1985, Sweden.

Transonic Systems, Inc., Access Flow & Recirculation Measured During Hemodialysis, Oct. 1994, N.Y.

C. Aldridge et al., "The Assessment of Arteriovenous Fistulae Created for Hemodialysis from Pressure and Thermal Dilution Measurements, Journal of Medical Engineering & Technology," vol. 8, No. 3, pp. 118–124, may/Jun. 1984, U.K.

C. Aldridge, et al., "Instrument Design for the Bedside Assessment of Arteriovenous Fistulae in Hemodialysis Patients", Proceedings EDTNA–ERCA, vol. 14, pp. 255–260, 1985, U.K.

Joseph J. Carr, "Integration of Decaying Exponential Sensor Output Signals", Sensors, pp. 28–34, Jul. 1989, Virginia.

J. Daugirdas, "The Fourth Annual Advanced Dialysis Technical Symposium", Dialysis & Transplantation, vol. 17, No. 8, pp. 432–433, Aug. 1988, Illinois.

Fresenius, "BTM 4008", Nov. 1993, Germany and translation from German to English.

Gambro, "Fistula Assessment Monitor FAM10," approximately 1985, U.K.

Gambro, "Fistula Assessment Monitor FAM10 Operator's Manual," approximately 1985, U.K.

Gambro, "Fistula Assessment Monitor FAM10 Service Manual," approximately 1985, Sidcup, Kent, U.K.

J.S. Gani et al., "Use of the Fistula Assessment Monitor to Detect Stenoses in Access Fistulae," (abstract) Australian Society of Nephrology, 1989, Australia.

Jonothan S. Gani, "Use of the fistula Assessment Monitor to Detect Stenoses in Access Fistulae," American Journal of Kidney Diseases, vol. XVII, No. 3, pp. 303–306, Mar. 1991, Newcastle, Australia.

R N Greenwood et al. "Assessment of Arteriovenous Fistulae From Pressure and Recirculation Studies. Clinical Experience in 186 Fistulae", Abstract p. 106, 1985, London, U.K.

R.N. Greenwood et al., "Assessment of Arteriovenous Fistulas From Pressure and Recirculation Studies: Clinical Experience in 215 Upper Limb Fistulas, EDTA–ERA", vol. 22, pp. 296–302, 1985, London, U.K.

R N Greenwood et al., "Assessment of Arteriovenous Fisulae from Pressure and Thermal Dilution Studies: Clinical Experience in Forearm Fistulae," Clinical Nephrology, vol. 23, No. 4, pp. 189–197, 1985, U.K.

L. Goldstein et al., The Assessment of Arteriovenous Fistulae From Pressure and Recirculation Studies:, Porc EDT-NA–ERCA, vol. 14, pp. 207–215, 1985, United Kingdom.

Lynn W. Hart et al., A Noninvasive Electromagnetic Conductivity Sensor for Biomedical Applications:, IEEE Transactions on Biomedical Engineering, vol. 35, No. 12, pp. 1011–1022, Dec. 1988, Maryland.

Robert L. Hester et al., "The Determination of Hemodialysis Blood Recirculation Using Blood Urea Nitrogen Measurements" American Journal of Kidney Diseases, vol. XX, No. 6, pp. 598–602, Dec. 1992, Mississippi.

M. Kramer et al., "Automated Measurement of Recirculation," EDTNA–ERCA, Journal, vol. XIX, No. 2, Apr. 1993.

Matthias Kramer et al., "A Device for Control of Thermal Parameters and Recirculation Measurement in Hemodialysis," Nov., 1992, Germany.

Transonic Systems, Inc., "Transonic Hemodialysis Monitor Measures Access Flow Recirculation Cardiac Output Routinely during Dialysis," Apr. 1995.

Nikolai M. Krivitski, "Novel Method to Measure Access Flow during Hemodialysis by Ultrasound Velocity Dilution Technique", Jul. 27, 1995, ASAIO Journal, pp. 0014–0018.

Thomas A. Depner and Nikolai M. Krivitski, "Clinical Measurement of Blood Flow in Hemodialysis Access Fistulae and Grafts by Ultrasound Dilution," Jul. 27, 1995, ASAIO Journal, pp. 0018–0022.

Thomas A Depner et al., "Hemodialysis Access Recirculation Measured by Ultrasound Dilution", Jul. 27, 1995, ASAIO Journal, pp. 0022–0026.

N.M. Krivitski, "Novel Method to Measure Access Flow Duing Hemodialysis by Ultrasound Dilution(UD)", ASAIO Journal 1995.

Nikolai M. Krivitski, "Theory and Validation of Access Flow Measurement by Dilution Technique During Hemodialysis", Kidney International, vol. 48 (1985), pp. 244–250.

N.M. Krivitski, "Accuracy of Ultrasound Dilution Method to Measure Access Flow (AF) in Hemodialysis", XIIIth International Congress of Nephrology, Abstract, 1995.

Nikolai Krivitski, Ph.D. "New Method to Measure Recirculation (RC) and Access Flow During Hemodialysis (HD)" American Nephrology Nurses' Association $26^{th}$ National Symposium Exhibitor Continuing Education Program, Abstract 1995.

T. Depner, "Changes in Access Blood Flow(Qac) and Appearance of Recirculation (RC) During Hemodialysis", XIIIth International Congress of Nephrology, Abstract., 1995.

T.A. Depner et al., "Hemodialysis Access Recirculation (RC) Measured by Ultrasound Dilution", ASAIOJournal 1995 Abstracts, Supplement to Jan.–Mar. 1995 vol. 41, No. 1, p. 80.

T.A. Depner and N.M. Krivitski, "Clinical Measurement of Blood Flow in Hemodialysis Access Fistulae and Grafts by Ultrasound Dilution", ASAIO Journal 1995 Abstracts, Supplement to Jan.–Mar. 1995 vol. 41, No. 1, p. 80.

Transonic Systems, Inc., "Recirculation, Access Flow Measurements," 1995, pp. 19–26.

N.M. Krivitski, "Cardiac Output Measurement in Extracorporeal Systems by Ultrasound Velocity Dilution," ASAIO Abstracts, 1994, p. 82.

Jeffrey Sands et al., "The Effect of Doppler Flow Screening Studies and Elective Revisions on Dialysis Access Failure", Reprint from ASAIO Transactions, Jul.–Sep., 1992, pp. M524–M527.

John L. Nosher, "Death Taxes, and Vascular Access Dysfunction, Seminars in Dialysis," vol. 4, No. 2, pp. 67–68, Apr.–Jun. 1991, New Jersey.

In–Line Diagnostics (brochure) "Improve the Clinical Outcome of Every Patient!", four pages, (undated).

In–Line Diagnostics (brochure) "Non–Invasive Blood Volume Monitoring", two pages, 1994.

In–Line Diagnostics (brochure) "The Crit–Line System", two pages, (undated).

John D. Bower and Thomas G. Coleman, "Circulatory Function During Chronic Hemodialysis", vol. XV Trans. Amer. Soc. Artif. Int. Organs, 1969, pp. 373–377.

C. Aldridge, "The Use and Management of Arteriovenous Fistulae Fact and Fiction," EDTNA ERCA, Journal SVII–4, pp. 29–35, Oct. 1991, United Kingdom.

R.L. Hester et al., "Non–Invasive Measurement of Recirculation in Dialysis Patient," Abstract No. 7, Jul. 1992.

Robert L. Hester et al., "Non–Invasive Determination of Recirculation in the Patient on Dialysis," ASAIO Journal, pp. M190–M193, 1992, Mississippi.

R.N. Greenwood and W. R. Cattell, "Single Needle Dialysis," Journal of Medical Engineering & Technology, vol. 6, No. 3 (May/Jun. 1982), pp. 93–98.

K. Konner, H M Karnahl, "Transvenous Serial Xero–Arteriography: A New Non–Invasive Angiographic Method for AV–Fistulas in Haemodialysis Patients," Proc EDTA (1981) vol. 18, pp. 305–309.

L. Forsberg, T. Holmin and E. Linstedt, "Quantitative Doppler And Ultrasound Measurements In Surgically Performed Arteriovenous Fistulas Of the Arm," Acta Radiologica Diagnosis 21 (1980) Fasc.6, pp. 769–771.

* cited by examiner

ACCESS FLOW MONITORING USING REVERSAL OF NORMAL BLOOD FLOW

FIELD OF THE INVENTION

This invention relates to measurement of recirculation rate and flow rate in a fistula. More particularly, this invention relates to measurement of the fistula fluid flow rate and recirculation rate during a medical procedure without opening a closed aseptic blood loop.

BACKGROUND OF THE INVENTION

In many medical situations it is desirable to quantitatively determine, or measure, the recirculation rate or the flow rate of a biological or medical fluid to increase the benefits of a therapeutic treatment, or alternatively, to decrease the time required for the treatment. This information is also useful for diagnostic purposes. For example, hemodialysis (herein "dialysis") is an uncomfortable medical procedure. It is, therefore, widely recognized as desirable for therapy to minimize the amount of time required to complete the dialysis procedure while still achieving a desired level of treatment.

In dialysis, a joint is typically surgically created between a vein and artery of a patient. This joint provides a blood access site where a blood loop, comprising an inlet or arterial line to a dialysis apparatus and an outlet or venous line from the dialysis apparatus, may be connected to the patient. The patient's blood flows through the joint from the artery to the vein. The inlet line draws blood to be treated from the patient through a first cannula inserted into the joint, while the outlet line returns treated blood to the patient through a first cannula inserted into the joint, while the outlet line returns treated blood (i.e., after dialysis), to the patient through a second cannula inserted into the joint between the first cannula and the vein. The joint may be an arteriovenous fistula, which is a direct connection from one of the patient's arteries to one of the patient's veins. Alternatively, the joint may be a synthetic or animal organ graft connecting the artery to the vein. As used herein, the term "fistula" refers to any surgically created or implanted joint between one of the patient's veins and one of the patient's arteries, however created. More generally, the terms "shunt" or "access" refer to any similar joint, either in a hemodialysis patient or in another area.

A portion of the treated blood, after being returned to the patient by the outlet line, may recirculate within the fistula and commingle with untreated blood being withdrawn from the patient by the inlet line. The result is a decrease in the efficiency of the therapy, as some of the volume of blood in the inlet line has already been treated. The inefficiency in turn requires a longer treatment period with negative effects upon the patient. This recirculation and the resulting commingling is dependent in part on the rate at which the blood is withdrawn from and returned to the patient. In order to select the most efficient flow rate and thus achieve the quickest possible treatment time, it is desirable to know the proportion of recirculated treated blood in the blood being withdrawn from the patient by the inlet line.

A method and apparatus for quantitatively determining the degree of recirculation in a fistula is described in U.S. Pat. No. 5,510,717, incorporated herein by reference in its entirety. In the method disclosed in the patent, a bolus of marker fluid having a conductivity different from that of blood is injected through an injection site in the outlet line. A differential conductivity monitor quantitatively measures the degree of recirculation in a fistula by comparing the conductivity of blood entering the fistula to the conductivity of blood being withdrawn from the fistula. This measurement is made as blood flows in the predominant direction from artery to vein. Conductivity is not the only property used in the prior art for sensing recirculated blood. Among other fluid properties utilized for the measurement of recirculated blood are temperature of the fluid and speed of conduction of sound. Some of these measurement techniques also involve injection of a bolus of marker material into the blood flow. For all the above methods of detecting recirculating blood, the techniques for handling the blood loop remain essentially the same.

Measurement of the fistula's flow rate is also desirable. In the patient, the fistula gradually loses its ability to efficiently transport blood from artery to vein. Fat and other deposits build up within the fistula and flow is gradually reduced. Eventually, the fistula must be replaced. This repetitious replacement can account for half the long term cost of dialysis treatment. In the interest of making these replacements as infrequent as possible, it is necessary to know whether the fistula flow rate is adequate. It can be readily appreciated that ascertaining the flow rate through the fistula is very important to long term care of the patient.

The flow rate through the fistula or the access flow rate ("Q-access") can be determined utilizing the same equipment and procedures used for monitoring of the recirculation rate, but with a reversed flow of blood to the fistula. To measure Q-access the inlet line is disconnected from the first line and connected to the second cannula while the outlet line is disconnected from the second cannula and connected to the first cannula. Blood is withdrawn from the fistula at a location downstream of the location at which it is returned to the fistula. By injecting a bolus of a marker fluid having a property such as conductivity different from that of blood, and measuring and comparing the values of that property in the inlet and outlet lines, the Q-access or access flow rate of the dialysis apparatus may be determined.

This reversal of the blood flow is accomplished by manually switching the tubing and cannula which connect the dialysis apparatus to the patient, or switching the lines at a point removed from the patient. This switching of the lines is well known in the prior art, regardless of the equipment or exact blood property being used to measure the recirculation rate and access flow rate.

Even in situations where it is desired to measure Q-access without measuring recirculation flow, this manual switching is required as the desirable flow of blood into and out of the fistula for dialysis treatment is the opposite of that required for measuring Q-access.

The switch of tubing and cannulae is a source of danger to the patient and to health care personnel. Normally, the dialysis machine, fistula, and associated tubing provide a closed loop or closed aseptic system. Switching of the tubing presents risks that aseptic techniques may be compromised by the operator. Ultrasonic air bubble protection may be lost. Blood may be sprayed or spilled onto the operator, raising the risk of blood borne infection. Finally, when dealing with open blood lines, there is a chance of exsanguination of the patient.

It is against this background that the significant advances of the present invention developed.

SUMMARY OF THE INVENTION

A significant aspect of the present invention is a method and apparatus that permits monitoring access flow while avoiding the disconnection and reconnection of blood lines.

In accordance with this aspect of the invention, the blood lines remain attached in the normal configuration, as for blood flow in a first direction throughout the dialysis procedure. The blood flow is reversed within the blood loop without compromising the aseptic integrity of the blood loop. Blood is flowed though the blood loop in the first direction by the action of a pump, such as a peristaltic pump. By reversing the action of the peristaltic pump, the flow of blood in the blood loop is reversed and the blood flows in a second direction. With the blood flow reversed, blood flows through the normal blood outlet line into the fistula and through the normal blood inlet line out from the fistula.

An injection site is provided in the blood inlet line, if needed, to inject a bolus of marker fluid into the inlet line.

A further aspect of the present invention is a method and apparatus whereby blood is flowed through the blood loop in the second direction by action of a valve assembly.

A further aspect of the present invention is a method and apparatus which allows automatic monitoring and/or control of the injection of the marker fluid.

A further aspect of the invention is a method and apparatus which detects air bubbles in the inlet or arterial line.

Further aspects of the present invention will be apparent from the detailed description of the preferred embodiment and the claims.

DETAILED DESCRIPTION OF THE PREFERRED EMBODIMENT

The present invention will be described by reference to FIGS. 1 to 6. Like reference numerals in the drawings denote like elements.

Figure 1:
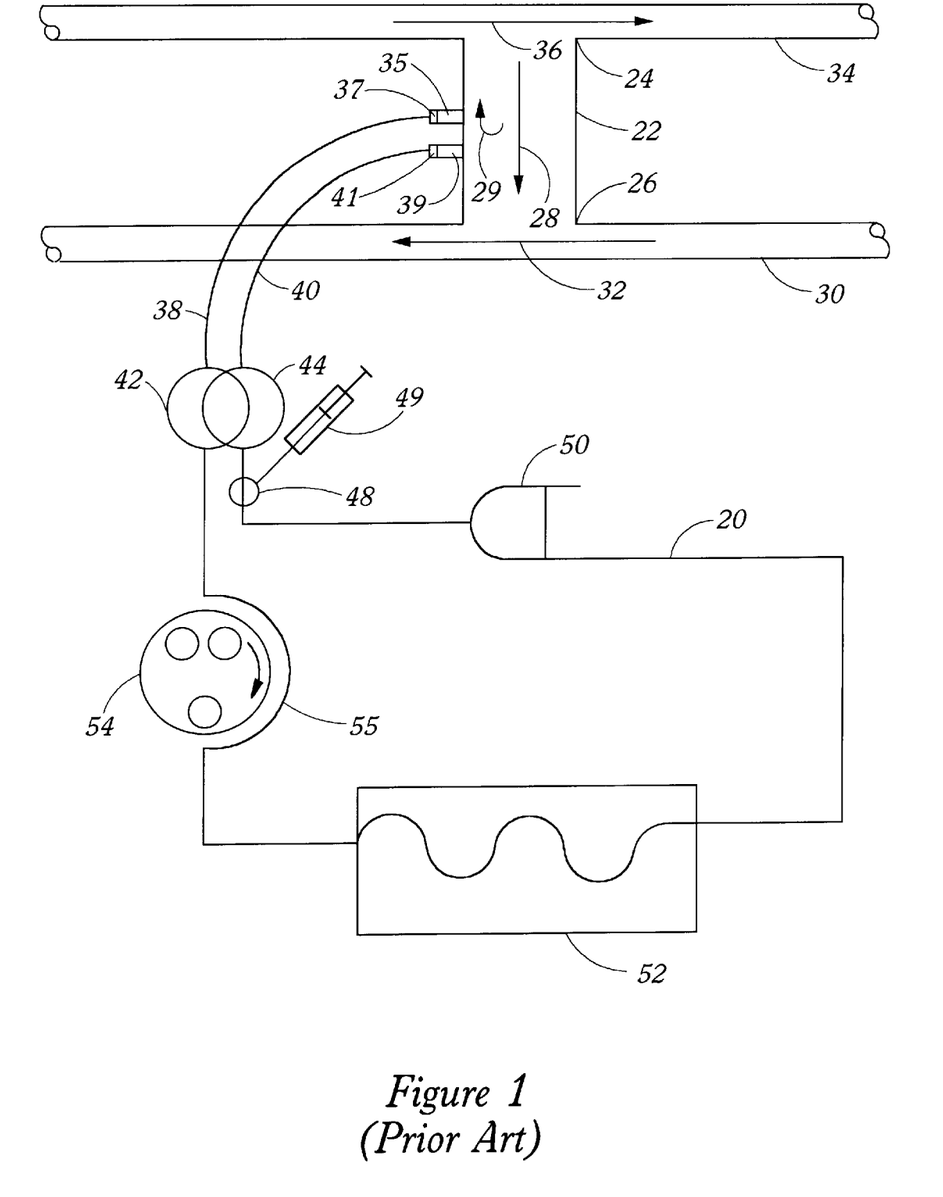
FIG. 1 is a schematic diagram not to scale of the blood loop of a dialysis system in accordance with the prior art.

FIG. 1 illustrates a dialysis system blood loop 20 in accordance with the prior art. The blood loop 20 is located outside a body of a dialysis patient (not shown). A fistula 22 having an arterial end 24 at an artery 34 and a venous end 26 at a vein 30 is surgically formed in the patient. The predominant fistula 22 blood flow direction is shown by fistula blood flow arrow 28. Over time the fistula 22 normally suffers from increasing recirculation of flow indicated by recirculation flow arrow 29 and a gradual decrease in the fistula blood flow 28 through it. Both of these values may be ascertained in order to maximize the efficiency of treatment. Recirculation flow 29 causes some treated blood to flow with the untreated blood through the blood loop 20, diluting the untreated blood flow through the apparatus and increasing the time of treatment. Decreased blood flow in the fistula also increases the time needed for treatment of the blood. Blood flow in the vein 30 is indicated by venous blood flow arrow 32 and blood flow in the artery 34 is indicated by arterial blood flow arrow 36.

The terms "inlet" and "outlet" used hereafter are taken as defined for the blood loop 20 during the time the blood is being dialyzed, i.e., while the patient is being treated. The blood loop 20 comprises an inlet cannula 35 connected to an inlet or arterial line 38 of the blood loop 20 by an inlet connector 37 which draws fluids from near the arterial end 24 of the fistula 22, and an outlet cannula 39 connected to an outlet or venous line 40 by an outlet connector 41 which returns treated blood to near the venous end 26 of the fistula 22. The blood loop 20 also comprises an inlet monitoring device 42, and outlet monitoring device 44, a bolus outlet injection point 48, a bubble trap 50, a fluid treatment device such as a dialyzer 52 and a peristaltic pump header 55. The blood loop 20 may also be comprised of other elements (not shown) as desired for the particular procedure.

Inlet and outlet monitoring devices 42 and 44 may be a differential conductivity monitor as described in U.S. Pat. No. 5,510,717 or may comprise a temperature, sound transmission (including ultrasonic) or other physical or chemical property monitor.

In a dialysis treatment, blood is drawn by a peristaltic pump 54 of a dialysis apparatus from the fistula 22 through the inlet cannula 35, inlet connector 37 and inlet line 38, through the inlet monitoring device 42, through a pump header 55, through the dialyzer 52, where it is treated, and returned through the bubble trap 50, the outlet bolus injection point 48, the outlet monitoring device 44, the outlet line 40, the outlet connector 41 and outlet cannula 39 to the fistula 22.

To measure recirculation, a bolus of a marker fluid 49 is injected into the treated blood through the outlet bolus injection point 48. The marker fluid is selected to alter one or more physical, optical, electrical or chemical properties of the blood. Outlet monitoring device 44 measures the value of the property in the outlet line 40 after the injection of a bolus of marker fluid. The inlet monitoring device 42 measures the value of the property in the inlet line. Comparison of the two values measured by the two monitoring devices 42 and 44 allows quantitative determination of the degree of recirculation occurring in the fistula 22 by known techniques while blood flows through the blood loop 20 in the course of being dialyzed.

Figure 2:
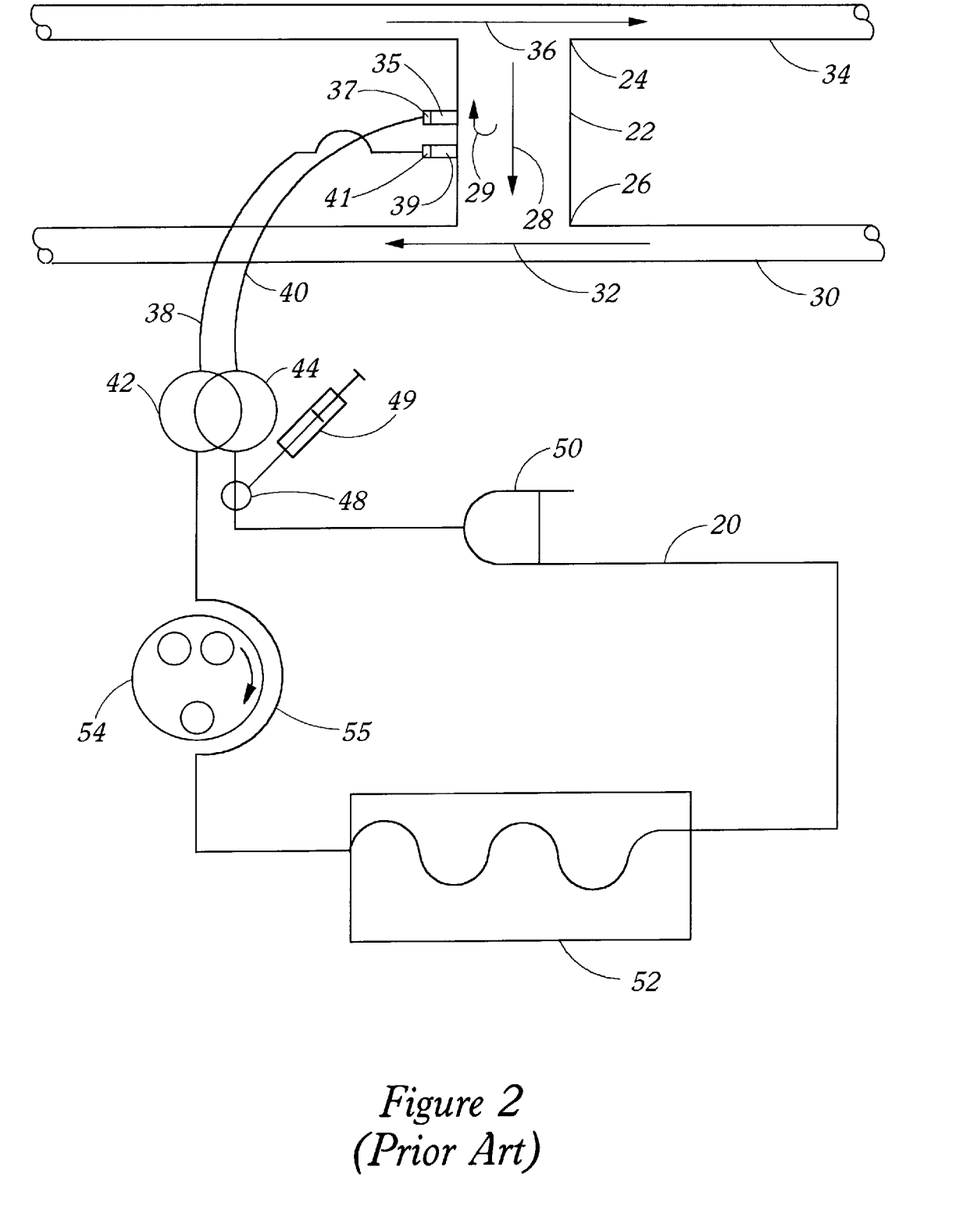
FIG. 2 is a schematic diagram not to scale of the blood loop of a dialysis system using a prior art configuration to measure Q-access.

FIG. 2 illustrates the prior art method of measuring access flow or Q-access through the fistula. In the prior art method, dialysis treatment is stopped for the measurement of Q-access. The outlet line 40 is disconnected from the outlet connector 41 and the inlet line 38 is disconnected from the inlet connector 37. The outlet line 40 is then connected to the inlet connector 37 and the inlet line 38 is connected to the outlet connector 41. The peristaltic pump 54 is then started to draw blood from the venous end 26 of the fistula 22 through the outlet cannula 39, through the outlet connector 41, inlet line 38, inlet monitoring device 42 and pump header 55, to the dialyzer 52, returning the blood through the bubble trap 50, the outlet bolus injection point 48, the outlet line 40, the inlet connector 37, and the inlet cannula 35 to the arterial end 24 of the fistula 22. A bolus of marker fluid 49 is injected into the blood through the outlet bolus injection point 48. The marker fluid alters a property of the blood in the outlet line 40. Outlet monitoring device 44 and inlet monitoring device 42 measure the values of the property. By comparing the values of the property, a measurement of Q-access in the fistula may be made using known techniques. After Q-access is determined, blood flow in the blood loop 20 is again stopped and the sequence of connections and disconnections reversed to resume dialysis as shown in FIG. 1.

The present invention will now be described by particular reference to FIGS. 3 and 4.

Figure 3:
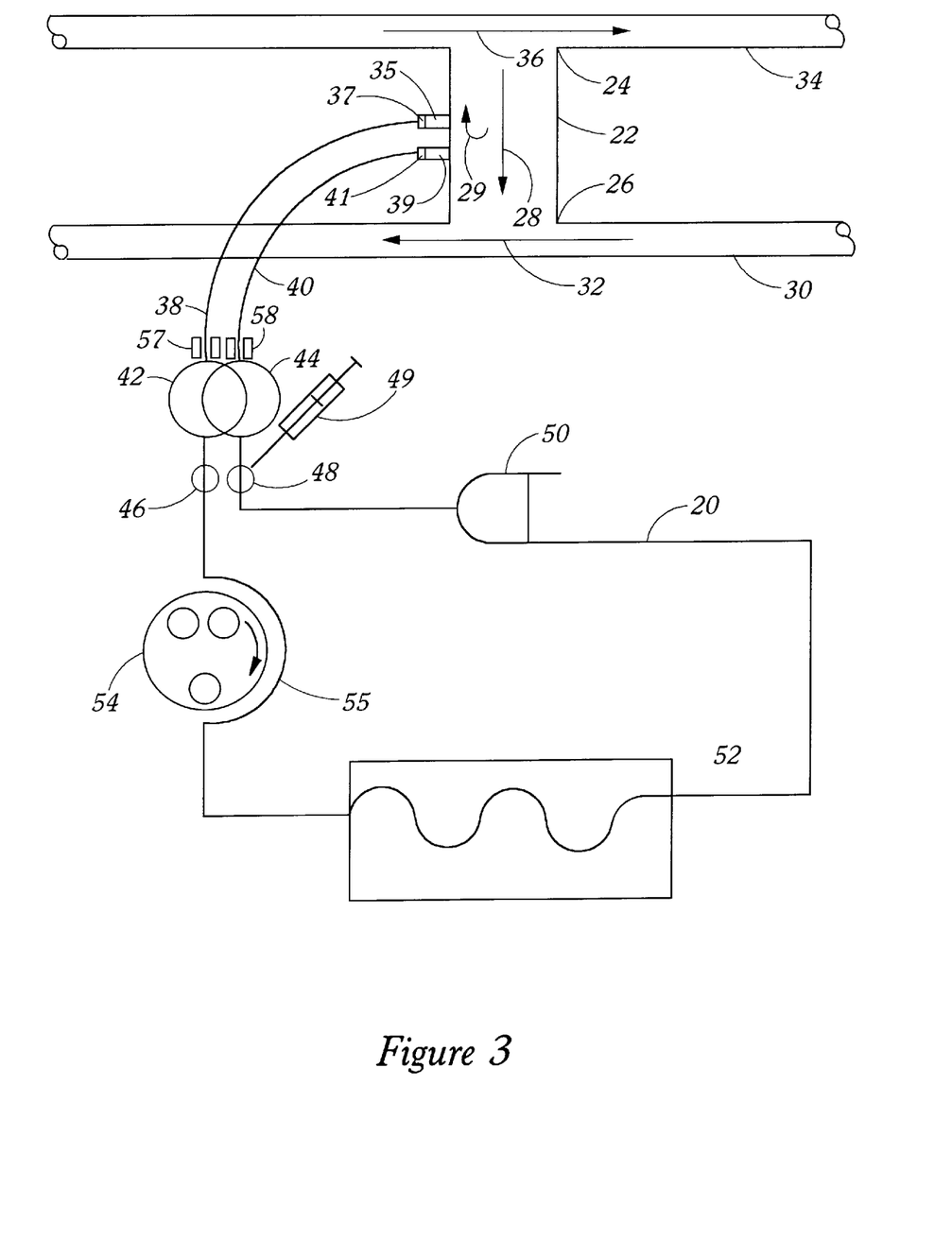
FIG. 3 is a schematic diagram not to scale of the blood loop of a dialysis system in accordance with the present invention.

Referring to FIG. 3, the blood loop 20' is similar to the blood loop 20 of the prior art with the addition of an inlet bolus injection site 46 and ultrasonic bubble detectors 57 and 58. Dialysis treatment and measurement of a degree of recirculation occur as described above with reference to FIG. 1 with the pump operating in a first (for example, clockwise) direction. The blood flow during dialysis treatment and measurement of recirculation is in a first direction.

Measurement of Q-access or access flow is accomplished without opening the closed loop by reversing the direction of operation of the pump 54 (for example, in the counter-clockwise direction). Blood flow, therefore, reverses its direction in the blood loop 20', and flows in a second direction opposite the first direction of blood flow for dialysis and recirculation. Blood is drawn from the venous end 26 of the fistula 22 through outlet cannula 39, the outlet connector 41 and into the outlet line 40, which now functions as a line leading into the blood loop 20 and through the outlet monitoring device 44 and bubble trap 50 to the dialyzer. Blood then flows from the dialyzer 52 through the pump header 55, the inlet bolus injection point 46, the inlet monitoring device 42, the inlet line 38, the inlet connector 37 and the inlet cannula 35 to the arterial end 24 of the fistula 22. A bolus of marker fluid 49,(see FIG. 4) is injected at the inlet bolus injection point 46. Comparison of the readings taken by the inlet monitoring device 42 and the outlet monitoring device 44 allows measurement of the fistula blood flow 28 by known techniques. The inlet line 38 remains throughout the procedure connected to the inlet cannula 35 at the arterial end 24 of the fistula 20, and the outlet line 40 remains throughout the procedure connected to the outlet cannula 39 at the venous end 26 of the fistula 20.

The inlet and outlet bolus injection sites may be any of several known types such as needle-pierceable self-sealing septa, needle-less split septa, or three way stopcocks, and of which may be adapted to accept a conventional syringe 49 for manual injection of the bolus of marker fluid. Alternatively, a syringe 49 may be connected to the blood loop at the bolus injection site and automatically actuated by a syringe pump of a known type.

Figure 5:
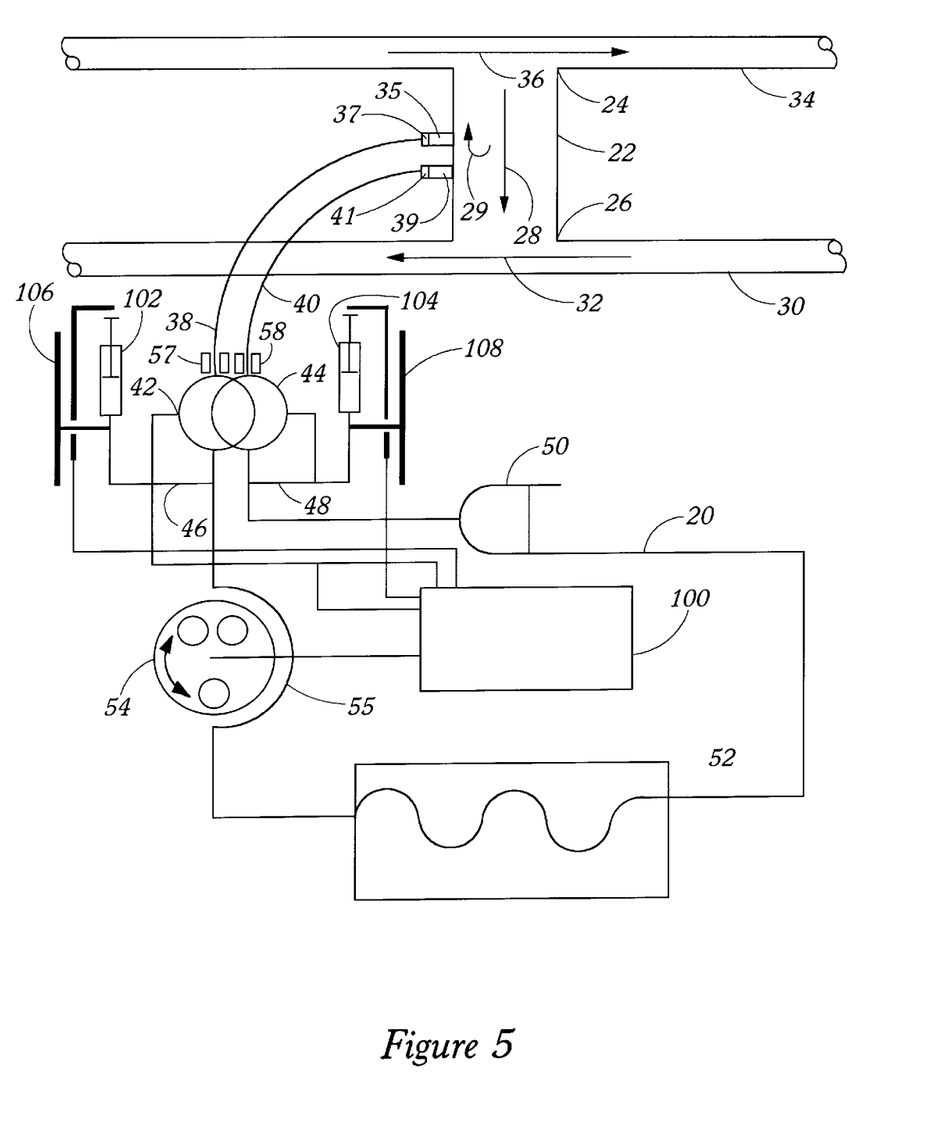
FIG. 5 is a schematic diagram not to scale of the present invention configured for automatic control, showing both the blood loop and the control circuitry of the controller for automatic control.

FIG. 5 illustrates an alternative embodiment of the present invention in which the measurement of recirculation flow 28 and Q-access 29 are more fully automated. A controller 100 is provided to control and interpret the measurements. The controller 100 may also perform other functions associated with the operation of the dialysis apparatus. The bolus injection sites 46' and 48' are "t " tubing connections. An inlet bolus syringe 102 is connected to the inlet bolus injection site 46 and an outlet bolus syringe 104 is connected to the outlet bolus injection site 48'. Each syringe 102 and 104 is loaded into a corresponding syringe pump 106 and 108 of the dialysis apparatus 21. The syringe pumps 106 and 108 may be of known types. The controller 100 is configured and programmed to control the action of the peristaltic pump 54 and the two syringe pumps 106 and 108 to initiate and perform the measurement of degree of recirculation flow and Q-access as described above. The controller 100 may also receive information signals from the property monitoring devices 42 and 44. The above discussed operations of the dialysis machine may be automated or semi-automated. The semi-automated modes could allow operator input at decision-making times, or could automate certain operations and not others.

Figure 4:
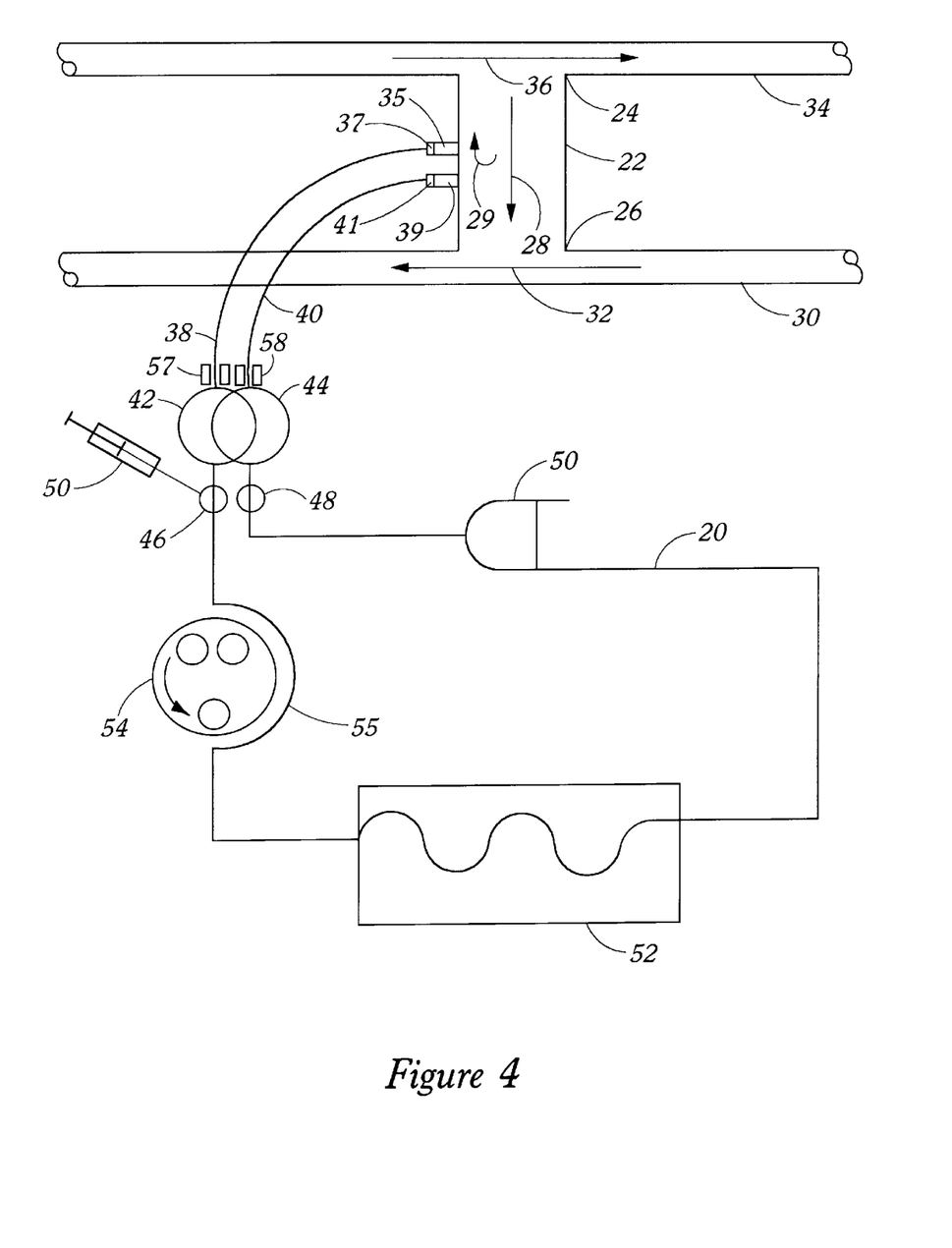
FIG. 4 is a schematic diagram not to scale of the blood loop of a dialysis system of the present invention configured to measure Q-access.

An ultrasonic bubble detector 57 shown in FIGS. 3–5 can also be placed in the arterial or inlet line 38. The ultrasonic bubble detector is to detect foam or air in the inlet line. Similarly, an ultrasonic bubble detector 58 may also be used in the venous or outlet line. The location of the ultrasonic bubble detector may be varied, however, it is preferable that it be after the injection site in the direction of flow for measurement of access flow. That is the ultrasonic bubble detector should be between the injection site 46, 46' and the fistula connection 35, 37. The ultrasonic bubble detector may be that shown in U.S. Pat. No. 5,394,732, incorporated herein in its entirety by reference, or of another well known type.

It will be apparent to those skilled in the art that the present invention will function in substantially the same way regardless of the known physical blood property being measured, the marker fluid used to alter that property, or the type of measuring devices used to measure the values of the property. For example, the known physical property to be measured may include, but is not limited to, temperature, sound transmission including ultrasonic transmission.

In the preferred embodiment, a second ultrasonic bubble trap, (not shown), may also be placed on the inlet line 38 if necessary to provide bubble protection for flow in either direction. Other known equipment can also be added to inlet line 38 or outlet line 40 as necessary.

It will be apparent to those skilled in the art that there are other ways available to cause blood flow in the second direction without disconnection of the inlet and outlet lines.

Figure 6:
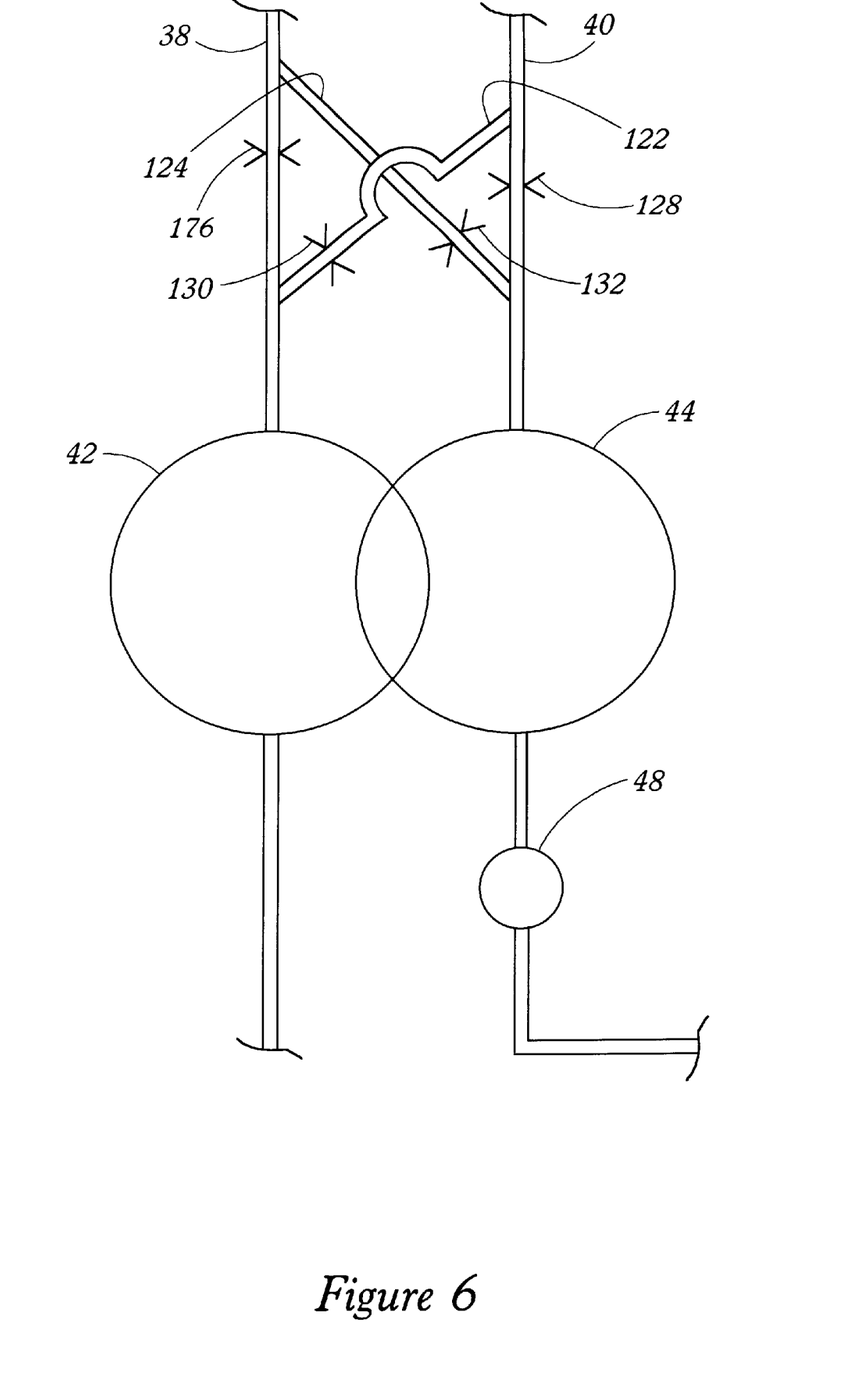
FIG. 6 is a schematic diagram not to scale of a portion of the blood loop shown in FIGS. 3–5, illustrating a valve assembly to reverse the blood flow.

FIG. 6 illustrates one such method of reversing blood flow without reversal of the pump. The valve assembly of FIG. 6 allows for reversal of the blood flow without compromising the closed aseptic blood loop. The valve assembly may be placed between the monitoring devices 42, 44 and the respective inlet and outlet connectors 37 and 41. A portion of the tubing loop showing the valve assembly is illustrated in FIG. 6.

The tubing set in this embodiment further comprises an inlet bypass 122 from the inlet line 38 to the outlet line 40, and an outlet bypass 124 from the outlet line 40 to the inlet line 38. An inlet bypass pinch valve 130 keeps the inlet bypass 122 closed during operation with blood flow in the first direction. An outlet bypass pinch valve 132 keeps the outlet bypass 124 closed during operations with blood flow in the first direction. An inlet pinch valve 126 and an outlet pinch valve 128 remain open during operations with blood flow in the first direction.

When it is desired to reverse blood flow, inlet pinch valve 126 and outlet pinch valve 128 are closed and inlet bypass pinch valve 130 and outlet bypass pinch valve 132 are opened, causing the flow in the second direction as discussed above.

As will be apparent to one skilled in the art, FIG. 6 depicts only one possible arrangement of tubing and valves which would allow reversal of blood flow. Other equivalents can be substituted within the scope of the present invention. It is further apparent that other known valves other than pinch valves can be used.

The preferred embodiment of the present invention has been described by reference to determination of flow characteristics in a surgically created fistula during or in conjunction with a hemodialysis procedure. It should be understood that the present invention is not so limited. The present invention may be used in a variety of medical and non-medical circumstances where it is desirable to determine flow characteristics without compromising the integrity of the fluid loop. Presently preferred embodiments of the present invention and many of its aspects, features and advantages have been described with a degree of particularity. It should be understood that this description has been made by way of preferred embodiment, and that the invention is defined by the scope of the following claims.

We claim:

1. Apparatus for measuring flow rate of a fluid through a fistula, the apparatus comprising a fluid loop having a first end connectable to the fistula and a second end connectable to the fistula wherein when the fluid loop is connected to fistula at the first and second ends the fistula and fluid loop form a closed fluid loop;

a pump for moving the fluid through the fluid loop in a first direction and a second direction opposite said first direction;

means for altering a property of the fluid in fluid loop; and first means for measuring the altered property of the fluid to determine the flow rate of the fluid through the fistula when connected after passage of the fluid through the fistula during movement of the fluid in one of the first or second directions.

2. The apparatus of claim 1 further comprising a fluid treatment device in the fluid loop.

3. The apparatus of claim 2 wherein the fluid treatment device comprises a dialyzer.

4. The apparatus of claim 1 wherein the means for altering the property of a fluid is located in the fluid loop on the opposite side of the fistula when connected from the means for measuring the altered property of the fluid.

5. The apparatus of claim 4 where in the means for altering a property of the fluid comprises means for injecting a bolus of marker fluid into the fluid to alter the property of the fluid.

6. The apparatus of claim 2 wherein said pump moves the fluid in said first direction for treatment of the fluid with the fluid treatment device and in said second direction for measurement of the altered property of the fluid.

7. The apparatus of claim 6 further comprising means for measuring recirculation of the fluid through the fistula when connected.

8. The apparatus of claim 7 wherein said means for measuring recirculation measures the recirculation of the fluid when the fluid is moving in said first direction.

9. The apparatus of claim 1 further comprising means for measuring recirculation of the fluid through the fistula when connected.

10. The apparatus of claim 9 further comprising second mean for measuring the altered property of the fluid during movement of the fluid opposite said one direction.

11. A method of measuring the flow rate of a fluid through a fistula in a closed fluid loop wherein the fluid normally flows in a first flow direction through the fistula and the closed fluid loop, the method comprising reversing the flow of fluid through the closed fluid loop and the fistula from the first flow direction to a second flow direction opposite the first flow direction while maintaining the closed fluid loop;

altering a property of the fluid prior to passage through the fistula in the second flow direction;

measuring the altered property of the fluid after passage through the fistula in the second flow direction.

12. The method of claim 11 further comprising measuring the property of the fluid prior to passage through the fistula in the second flow direction; and comparing the measurement of the property of the fluid prior to passage through the fistula to the measurement of the property after passage through the fistula to determine the flow rate through the fistula.

13. The method of claim 11 wherein the step of altering a property of the fluid further comprises injecting a bolus of marker fluid into the fluid to alter the property of the fluid.

14. The method of claim 13 wherein said step of altering the property of the fluid further comprises injecting a bolus of marker fluid to alter the property of the fluid.

15. A method of measuring recirculation of fluid through a fistula in a closed fluid loop and flow rate of the fluid through the fistula, the method comprising flowing the fluid in a first flow direction wherein the fluid leaves the fistula at one end of the fistula, passes through the closed fluid loop, and returns to the fistula at a second end of the fistula;

reversing the flow of fluid to a second flow direction opposite said first direction wherein the fluid flows from the closed fluid loop to the fistula at the second end of the fistula, passes through the fistula, and returns to the closed fluid loop from the first end of the fistula;

altering a property of the fluid;

measuring the altered property of the fluid after the fluid leaves the fistula when the fluid flows in the first flow direction to determine recirculation of the fluid through the fistula;

measuring the altered property of the fluid after the fluid passes through the fistula in the second flow direction to determine flow rate of the fluid through the fistula.

16. Dialysis apparatus wherein the dialysis apparatus is connectable to a fistula, the dialysis apparatus comprising a dialyzer for treating fluid passed therethrough;

a first tubing loop connected to the dialyzer and connectable to the fistula;

a second tubing loop connected to the dialyzer and connectable to the fistula wherein the fistula when connected, the first tubing loop, the dialyzer, and the second tubing loop form a closed fluid loop for passage of a fluid;

a pump in one of said tubing loops for moving fluid through the closed fluid loop wherein the pump moves the fluid in a first direction for treatment of the fluid by the dialyzer and in a second direction opposite said first direction;

first means for altering a property of the fluid when the fluid flows in the second direction;

first means for measuring the altered property of the fluid after passage of the fluid through the fistula when connected when the fluid flows in the second direction.

17. The dialysis apparatus of claim 16 wherein said first means for altering a property comprises a bolus for injecting marker fluid into the fluid to alter the property of the fluid.

18. The dialysis apparatus of claim 16 further comprising means for measuring recirculation through the fistula when connected, said means for measuring recirculation comprising second means for altering a property of the fluid when the fluid flows in the first direction; and second means for detecting said altered property of fluid when the fluid flows in said first direction.

19. The dialysis apparatus of claim 18 wherein said second means for altering a property of the fluid comprise a bolus for injecting marker fluid into the fluid to alter the property of the fluid.

20. Apparatus for measuring flow rate of a fluid through a fistula wherein the fluid normally flows through the fistula in a first direction, the apparatus comprising
a fluid loop having a first end connectable to a fistula and a second end connectable to the fistula wherein the fluid loop and the fistula when connected form a closed fluid loop;
means for reversing the fluid flow through the fluid loop from the first flow direction to a second flow direction opposite said first flow direction while maintaining the closed fluid loop;
means for altering a property of the fluid in the fluid loop;
means for measuring the altered property of the fluid to determine the flow rate of the fluid through the fistula when connected after passage of the fluid through the fistula when connected during movement of the fluid in one of the first or second flow directions.

21. The apparatus of claim 20 further comprising a fluid treatment device in the closed fluid loop.

22. The apparatus of claim 21 wherein the fluid treatment device comprises a dialyzer.

23. The apparatus of claim 20 wherein the means for altering the property of a fluid is located in the closed fluid loop on the opposite side of the fistula when connected from the means for measuring the altered property of the fluid.

24. The apparatus of claim 20 wherein the means for reversing direction of fluid flow comprises valve mean in the closed fluid loop reversing the fluid flow so that fluid enters the fistula when connected at one of its ends in the first flow direction and fluid exits the fistula when connected from said one end in the second flow direction.

25. The apparatus of claim 20 wherein the means for altering a property of the fluid comprises means for injecting a bolus of marker fluid into the fluid to alter the property of the fluid.

26. The apparatus of claim 22 wherein said means for reversing the fluid flow moves the fluid in said first flow direction for treatment of the fluid with the fluid treatment device and in said second flow direction for measurement of the altered property of the fluid.

27. The apparatus of claim 26 further comprising means for measuring recirculation of the fluid through the fistula when connected.

28. The apparatus of claim 7 wherein said means for measuring recirculation measures the recirculation of the fluid when the fluid is moving in said first direction.

29. The apparatus of claim 20 further comprising means for measuring recirculation of the fluid through said fistula when connected.

30. The apparatus of claim 29 further comprising second means for measuring the altered property of the fluid during movement of the fluid opposite said one direction.

31. The apparatus of claim 30 further comprising a bubble detector located in the closed fluid loop between the means for altering a property and the fistula when connected.

32. Apparatus for measuring flow rate of a fluid through a fistula, the apparatus comprising
a fluid loop having a first end connectable to a fistula and a second end connectable to the fistula wherein the fluid loop and the fistula when connected form a closed fluid loop;
a pump for moving the fluid through the closed fluid loop in a first direction and in a second direction opposite said first direction;
an injection site in the closed loop for passage of material into the fluid to alter the property of the fluid;
a monitoring device for measuring the altered property of the fluid to determine the flow rate of the fluid through the fistula when connected after passage of the fluid having the altered property through the fistula when connected in one of the first or second directions.

33. The apparatus of claim 31 further comprising a dialyzer for treating the fluid in the closed fluid loop.

34. The apparatus of claim 32 wherein said pump moves the fluid in said first direction for treatment of the fluid in the dialyzer and in said second direction for measurement of the altered fluid.

35. The apparatus of claim 33 further comprising a monitor device for measuring recirculation of the fluid through the fistula when connected in said first direction.

36. The apparatus of claim 33 further comprising a second injection site for injecting material to alter the property of the fluid for the measurement of recirculation in said second direction.

37. Dialysis apparatus for treating fluid connectable to a fistula having an arterial side and a venous side, the dialysis apparatus comprising
a dialyzer for treating the fluid;
an arterial line connected to the dialyzer and connectable to the fistula at the arterial side for passing the fluid between the fistula, when connected, and the dialyzer;
a venous line connected to the dialyzer and connectable to the fistula at the venous side;
an ultrasonic bubble detector in the arterial line for detecting bubbles in the fluid.

38. The dialysis apparatus of claim 37 further comprising an injection site in the arterial line for injecting a material into the fluid as it passes through the arterial line wherein the material alters the property of the fluid.

39. The dialysis apparatus of claim 38 further comprising a detector in the venous line for detecting the altered property of the fluid.

* * * * *